United States Patent [19]

Wilson

[11] 4,281,207

[45] Jul. 28, 1981

[54] ALDEHYDE-CONTAINING VINYLARYL ETHERS

[75] Inventor: John C. Wilson, Rochester, N.Y.

[73] Assignee: Eastman Kodak Company, Rochester, N.Y.

[21] Appl. No.: 88,705

[22] Filed: Oct. 26, 1979

Related U.S. Application Data

[62] Division of Ser. No. 928,138, Jul. 26, 1978, Pat. No. 4,225,689.

[51] Int. Cl.$^3$ .................. C07C 47/232; C07C 47/548
[52] U.S. Cl. ..................................... 568/433; 568/442
[58] Field of Search ............................... 568/433, 442

[56] References Cited

U.S. PATENT DOCUMENTS

| | | | |
|---|---|---|---|
| 2,724,723 | 11/1955 | Bock | 568/442 X |
| 2,815,377 | 12/1957 | Meiser et al. | 568/442 X |
| 3,058,953 | 10/1962 | McMaster | 568/647 |
| 3,362,997 | 1/1968 | Bolhofer | 568/442 |

*Primary Examiner*—Bernard Helfin
*Attorney, Agent, or Firm*—Arthur H. Rosenstein

[57] ABSTRACT

Disclosed herein are monomeric compounds having the formula (I):

$$CHR=CR^1-\text{Ar}-(CHR^2)_m-O-R^4-(CHR^3)_n-CHO$$

wherein:
R, $R^1$, $R^2$ and $R^3$ are independently hydrogen or alkyl having from 1 to 4 carbon atoms;
$R^4$ is arylene having 6 to 18 carbon atoms;
m is an integer from 1 to 4; and
n is an integer from 0 to 4.

These monomers can be homopolymerized or copolymerized with one or more other polymerizable monomers, and can particularly be copolymerized with those monomers having substituents which are susceptible to attack or degradation by a base. The resulting crosslinkable polymers are useful in relief image materials, such as photoresists and lithographic plates.

11 Claims, No Drawings

ALDEHYDE-CONTAINING VINYLARYL ETHERS

This is a division of application Ser. No. 928,138, filed July 26, 1978 and now U.S. Pat. No. 4,225,689.

BACKGROUND OF THE INVENTION

1. Field of the Invention

This invention relates to organic materials which are particularly useful in preparing polymers which are useful in the graphic arts. In one of its aspects, this invention relates to the use of such materials to prepare crosslinkable polymers which can be incorporated into radiation-sensitive elements to obtain a desirable combination or properties.

2. Description of the Prior Art

Conventional vinyldiaryl ether monomers and polymers formed therefrom are disclosed in U.S. Pat. No. 2,522,501, issued Sept. 19, 1950. The monomers are generally prepared by reacting a diaryl ether with acetyl chloride, forming a carbinol by reduction and dehydrating the resulting carbinol. Polymerization occurs when the monomers are heated in air at high temperatures. The disclosed monomers and the polymers prepared therefrom contain only unsubstituted aryl groups.

U.S. Pat. No. 3,055,947, issued Sept. 25, 1962, discloses vinylaryl ether monomers which are formed from the reaction (at 50° to 200° C.) of a haloalkyl aromatic halomethyl compound

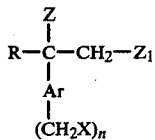

with an hydroxyl $R_1OH$ in the presence of a base metal catalyst, wherein:
  Ar is aryl;
  R is hydrogen or methyl;
  $R_1$ is hydrogen, alkyl, aryl or aralkyl;
  X is a halide;
  Z and $Z_1$ are either hydrogen or halide; and
  n is an integer of 1 to 3.

$R_1$ can also be a substituted aryl radical. This reference is typical of the art which shows the preparation of vinylaryl ether monomers by a reaction of a halogenated alkylbenzene with a phenol in a basic environment. One of ordinary skill in the art would not expect the disclosed method to be useful in the preparation of aldehyde-containing polymers because it is expected that the aldehyde would react with another aldehyde group or with the vinyl moiety thereby causing crosslinking.

It is desirable, however, to form vinylaryl ether monomers which have aldehyde substituents. Polymers formed from such monomers would provide crosslinking sites for further reaction with various reagents, such as amines and the like. In the reaction environment taught by U.S. Pat. No. 3,055,947, it is expected that any aldehyde-containing monomers would prematurely gel because of spontaneous crosslinking or polymerization. Furthermore, Ringsdorf et al, *Macromolecular Chem.*, 31, pages 27 through 49 (1959), disclose that vinyl compounds containing aldehyde groups polymerize to form insoluble polymers. One would expect a monomer containing an aldehyde group to form a crosslinked polymer during any conventional polymerization reaction.

Gibson et al, *J. Poly. Sci:Poly. Chem. Ed.*, 12, pages 2141 through 2143 (1974) and Gibson, *Macromolecules*, 8, pages 89 and 90 (1975), disclose that homopolymers and copolymers containing recurring units of vinylbenzyl phenylethers can be prepared by reaction of a phenol with a polymer containing recurring units of vinylbenzyl chloride in a basic environment. The phenyl groups can be substituted with a variety of radicals, including aldehydes. Not all copolymers containing aldehyde-substituted aryl ether units can be made by this method, however. In the basic environment of the phenol-poly(vinyl benzyl chloride) reaction, many copolymers containing certain substituents or functional groups hydrolyze or degrade. These substituents are reactive with and susceptible to attack or degradation by a base. By "susceptible to attack or degradation by a base" is meant an ability to undergo a chemical reaction with a base to form a species with a chemical structure different from that of the starting species. This ability includes such severe alterations that the degraded material cannot be restored simply by neutralizing the product species with an acid. Examples of such substituents and monomers containing them are given below in the Detailed Description of the Present Invention. Therefore, one could not make aldehyde-containing copolymers by the method described in the Gibson references.

Hence, a method of producing polymerizable vinylaryl ether monomers containing aldehyde groups, whereby gelation due to spontaneous polymerization and/or crosslinking is not allowed to occur, would be highly desirable. It would be further desirable to have a method of producing uncrosslinked polymers from such vinylaryl ether monomers. Such polymers could also contain recurring units of polymerizable monomers having functional groups which may be susceptible to attack or degradation by a base.

SUMMARY OF THE INVENTION

The present invention provides aldehyde-containing vinylaryl ether monomers which are easily prepared from readily available starting materials. Further, the present invention provides organic solvent-soluble polymers formed from the aldehyde-containing monomers. These polymers can comprise recurring units of monomers having substituents which are susceptible to attack or degradation by a base. The method of the present invention of preparing these polymers also avoids gelation.

The polymers of the present invention are useful in many applications, but are particularly useful with radiation-sensitive materials used in the graphic arts. These polymers with pendant aldehyde groups can be crosslinked with reagents such as amines to provide organic solvent-insoluble areas, such as in light exposed regions of a lithographic plate or a photoresist, thereby providing relief negative images.

An especially preferred use of these copolymers is for crosslinking with diamino compounds as described in copending U.S. patent application Ser. No. 872,852, filed Jan. 27, 1978 by Adin and Wilson and entitled "Photocrosslinkable Carbonyl-Containing Polymeric Composition and Elements".

One aspect of the present invention comprises a compound having the formula (I):

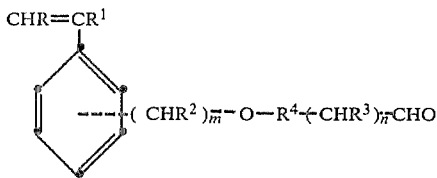

wherein:

R, $R^1$, $R^2$ and $R^3$ are independently hydrogen or alkyl having from 1 to 4 carbon atoms;

$R^4$ is arylene having 6 to 18 carbon atoms;

m is a integer from 1 to 4; and n is an integer from 0 to 4.

In another aspect of the present invention, a method of making a compound having formula (I) comprises reacting, in the presence of an acid acceptor, a compound having the formula:

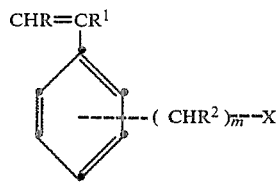

with a compound having the formula HO—$R^4$(—$CHR^3$)$_{\overline{n}}$—CHO, wherein:

X is a halide; and

R, $R^1$, $R^2$, $R^3$, $R^4$, m and n are as defined above.

Still another aspect of the present invention comprises an uncrosslinked polymer formed from:

(a) about 1 to 99 mole percent of one or more monomers having formula (I); and (b) from 1 to about 99 mole percent of one or more additional ethylenically unsaturated polymerizable monomers having substituents which are susceptible to degradation by a base.

In still another aspect of the present invention, a method of making an uncrosslinked polymer formed from:

(a) about 1 to 100 mole percent of one or more monomers having formula (I); and (b) from about 0 to about 99 mole percent of one or more additional ethylenically unsaturated polymerizable monomers, comprises:

(1) reacting, in the presence of an acid acceptor, a compound having the formula:

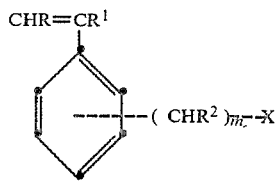

with a compound having the formula HO—$R^4$(—$CHR^3$)$_{\overline{n}}$CHO, wherein X is halide, and R, $R^1$, $R^2$, $R^3$, $R^4$, m and n are as defined above for formula (I); and (2) polymerizing the resulting aldehyde-containing monomer or copolymerizing the monomer with the one or more additional ethylenically unsaturated polymerizable monomers.

DETAILED DESCRIPTION OF THE INVENTION

In formula (I) describing the monomers of the present invention, R, $R^1$, $R^2$ and $R^3$ are independently hydrogen or alkyl having from 1 to 4 carbon atoms, such as methyl, ethyl, propyl, butyl, isopropyl, tert-butyl and the like. $R^4$ is arylene having from 6 to 18 carbon atoms, such as phenylene, naphthylene, anthrylene, biphenylylene, including substituted arylenes such as arylenes substituted with halides or lower alkyls as described for R, and those containing other substituents, such as nitro, alkoxy, and the like.

Exemplary monomers corresponding to formula (I) include o-, p- or m-formylphenyl vinylbenzyl ether, o-, p- or m-(2-formylethoxy)phenyl vinylbenzyl ether, 2-, 3- or 4-formylnaphthyl vinylbenzyl ether, (3- or 4-formyl-2-methylphenyl) vinylbenzyl ether, formylbiphenylyl vinylbenzyl ethers, and the like.

Monomers of the present invention which are preferred are those having formula (I) wherein R, $R^1$, $R^2$, and $R^3$ are all hydrogen, and most preferably when, additionally, m is 1 and n is 0. Preferred monomers are o-, p- and m-formylphenyl vinylbenzyl ethers.

The method of making monomers of formula (I) comprises reacting vinylaralkyl halides having the formula:

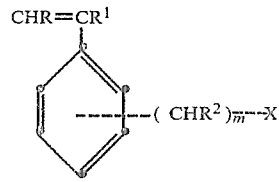

wherein:

R, $R^1$, $R^2$ and m are defined as in formula (I); and

X is halide, such as fluoride, chloride, bromide or iodide, with an aldehyde-containing hydroxyaryl having the formula HO—$R^4$(—$CHR^3$)$_{\overline{n}}$CHO wherein $R^3$, $R^4$ and n are defined as in formula (I).

Exemplary vinylaryl halides include o-, p- or m-vinylbenzyl chloride, o-, p- or m-vinylbenzyl bromide and the like. It is noted that many other halides could be used to prepare the monomers of formula (I). Similarly, exemplary hydroxyaryls include substituted or unsubstituted hydroxybenzaldehydes, salicylaldehydes, hydroxynaphthaldehydes, hydroxyanthraldehydes and the like.

The described reactants are reacted in the presence of an acid acceptor which is defined as a compound which neutralizes, or forms a salt with, the released halo acid. Exemplary acid acceptors include hydroxides, such as alkali metal hydroxides, alkaline earth metal hydroxides, quaternary alkyl ammonium hydroxides and the like; alkoxides, such as aluminum butoxide, calcium isopropoxide, sodium ethoxide and the like; carbonates, such as sodium carbonate, potassium carbonate, calcium carbonate and the like; pyridine; picoline; lutidine; weak base ion-exchange resins, such as Amberlite IR4B and Amberlite IR-45 (products sold commercially by Rohm and Haas Company) and the like; and others available in the art.

The reaction can take place in the presence of small amounts of polymerization inhibitors, such as o-, m- or p-dinitrobenzene, acetophenone, anilines, anthracene, p-benzoquinones, and the like and others available in the art.

Stoichiometrically, one mole of each of the reactants is required to produce one mole of ether and one mole of HX byproduct. It may be desired to provide an excess of one or the other of the reactants. Suitable molar ratios of the halide to the hydroxyaryl are in the range of from about 1:0.09 to about 1:1.5, and preferably of from about 1:0.09 to about 1:1.1.

If desired, a mutual inert solvent can be employed to dissolve the reactants or to serve as a heat transfer medium. The use of inert solvents is particularly desirable in a continuous operation. The products can be removed from the solvent by any suitable means, such as filtration, concentration and the like. The amount of solvent is not critical and can be in the range of from about 60 to about 95 weight percent of the reaction mixture, and preferably from about 70 to about 90 weight percent. Suitable solvents include alcohols, such as methanol, ethanol, isopropanol and the like; N,N-dimethylformamide; dimethyl sulfoxide and the like.

The reaction generally proceeds at reflux temperature, which is typically in the range of from about 20° to about 100° C., and preferably from about 70° to about 90° C. The reaction pressure can be from subatmospheric or superatmospheric pressures of about 1000 psig. Typically, the reaction is carried out at atmospheric pressure.

The reaction time is a function of reaction temperature and the particular reactants employed. Generally, reaction times are in the range of from about 15 to about 25 hours, but shorter times can be employed with more active reactants, and longer times for less active reactants.

Particular reaction conditions are illustrated in Examples 1 through 3 below in the preparation of particular monmeric ethers of the present invention.

The aldehyde-containing monomeric ethers of the present invention are useful in making the uncrosslinked polymers of the present invention. Preferably, these polymers are organic solvent soluble. These polymers can be crosslinked and used in elements in which it is desired to have organic solvent removable uncrosslinked regions and organic solvent resistant crosslinked regions as in negative image lithographic plates.

, These polymers are formed from about 1 to about 100 mole percent of one or more monomers having formula (I). Preferred polymers are those containing units of the preferred monomeric ethers discussed earlier.

In addition, the polymers can comprise from 0 to about 99 mole percent of recurring units derived from one or more additional ethylenically unsaturated polymerizable monomers, each containing, for example, at least one —CH=C< or CH$_2$=C< group. Exemplary monomers include vinyl esters, such as vinyl acetate, vinyl butyrte and the like; vinyl amides, such as acrylamide, methacrylamide, N-methylacrylamide, N-isopropylmethacrylamide and the like; vinyl nitriles, such as acrylonitrile, methacrylonitrile, 3-butenenitrile and the like; vinyl ketones, such as methyl vinyl ketone, diacetone acrylamide and the like; vinyl halides, such as vinyl chloride, vinyl bromide vinylidene chloride and the like; vinyl ethers, such as methyl vinyl ether, allyl methyl ether, allyl phenyl ether and the like; unsaturated acids or functional derivatives thereof, such as acrylic acid, methacrylic acid, methyl acrylate, butyl methacrylate, 2-dimethylaminoethyl methacrylate, 2-ethylhexyl acrylate, 2-hydroxyethyl methacrylate and the like; olefins and diolefins, such as ethylene, propylene, butadiene, isoprene, 1,1-diphenylethylene and the like; vinyl aromatics, such as styrene, α-methylstyrene, p-chlorostyrene and the like; 4,4,9-trimethyl-8-oxo-7-oxa-4-azonia-9-decene-1-sulfonate; N-vinylsuccinimide; N-vinylphthalimide; N-vinylpyrazolidone; and others available to those skilled in the art.

In a preferred embodiment of the present invention, the novel organic solvent soluble uncrosslinked polymers are formed from:

(a) about 1 to about 99 mole percent of one or more monomers having formula (I); and (b) about 1 to about 99 mole percent of one or more additional ethylenically unsaturated polymerizable monomers having substituents which are susceptible to degradation by a base.

In general, such monomers are those which have substituents that would undergo such reactions as ester interchange, ring openings, dehydrohalogenation, Hofmann elimination, ion exchange, displacement, alkylation, anhydride ring opening, salt formation, esterification and hydrolysis in a basic environment. These reactions are described in detail in general organic chemistry textbooks, including Morrison and Boyd, *Organic Chemistry*, 2nd Ed., Allyl and Bacon, Inc., 1966, and March, *Advanced Organic Chemistry:Reactions, Mechanisms, and Structure*, McGraw-Hill Co., 1968, hereby incorporated herein by reference.

Exemplary of polymerizable monomers having substituents which are susceptible to degradation by a base are vinyl esters, such as vinyl acetate, vinyl butyrate and the like; vinyl amides, such as acrylamide, methacrylamide, 3-acrylamidopropane-1-sulfonic acid, heterocyclic monomers such as N-vinyl-2-pyrrolidone, 2-phenyl-1-vinylimidazole, N-vinylsuccinimide and the like; vinyl halides, such as vinyl chloride, vinyl bromide, vinylidene chloride, vinylbenzyl chloride, 3-chloroprene and the like; vinyl nitriles, such as acrylonitrile, methacrylonitrile and the like; vinyl ketones, such as methyl vinyl ketone and the like; unsaturated acids or functional derivatives thereof, such as acrylic acid, methacrylic acid, crotonic acid, acanitic acid, α-chloroacrylic acid, maleic acid, citraconic acid, fumaric acid, methyl acrylate, isobutyl methacrylate, crotonyl acrylate, 2-chloroethyl methacrylate, 2-hydroxyethyl methacrylate, maleic anhydride, itaconic anhydride and the like; and sulfonamido-containing monomers, such as N-1-butyl-N-4-methacryloylsulfanilamide, N-(p-tolylsulfonyl)carbamic acid(maleinimido)methyl ester, N-butyl-4-methacryloyloxybenzenesulfonamide and the like. Mixtures of these monomers can be used, if desired.

Most preferably, the polymers of the present invention comprise recurring units derived from sulfonamido-containing monomers.

Although the amount of monomeric ether incorporated into the polymers of the preferred embodiment of the present invention can vary from about 1 to about 99 mole percent, preferably the amount is from about 20 to about 90 mole percent. The preferred amount of additional ethylenically unsaturated polymerizable monomers is from about 10 to about 80 mole percent.

Exemplary polymers of the present invention include poly(o-, m- or p-formylphenyl vinylbenzyl ether), poly-(o-, m- or p-formylphenyl vinylbenzyl ether-co-methyl methacrylate), poly(o-, m- or p-fomylphenyl vinylbenzyl ether-co-N-1-butyl-N-4-methacryloylsulfanilamide), poly[o-, m- or p-formylphenyl vinylbenzyl ether-co-N-(p-tolylsulfonyl)carbamic acid(maleinimido)- methyl ester], poly(o-, m- or p-formylphenyl vinylbenzyl ether-co-methyl vinyl ketone), poly-(o-, m- or p-formylphenyl vinylbenzyl ether-co-N-butyl-p-methacryloyloxybenzenesulfonamide), poly(o-, m- or p-formylphenyl vinylbenzyl ether-co-N$^1$-ethyl-N$^4$-methacryloylsulfanilamide), poly(o-, m- or p-formylphenyl vinylbenzyl ether-co-p-methanesulfonamidostyrene) and poly[o-formylphenyl vinylbenzyl ether-co-N-(2,6-dihydroxyphenyl)acrylamide-co-2-(methacryloyloxy)ethyltrimethylammonium methosulfate].

The method of making the polymers of the present invention comprises two steps, the first being that of making the aldehyde-containing monomeric ethers. The second step comprises homopolymerization of the monomeric ethers, copolymerization with each other, or copolymerization with the additional ethylenically unsaturated polymerizable monomers.

Polymerization can be carried out using techniques available to those skilled in the polymer chemistry art, including bulk, suspension, emulsion, solution and continuous techniques. Preferably, it is carried out in organic solvent solutions comprising solvents such as p-dioxane, N,N-dimethylformamide, tetrahydrofuran, dimethylsulfoxide and the like and most preferably in p-dioxane.

The temperature at which the polymers of the present invention are prepared is subject to wide variation, since this temperature depends upon such variable features as the specific initiator and monomers used, duration of heating, pressure employed and like considerations. However, the polymerization temperature generally does not exceed about 110° C., and most often it is in the range of from about 40° to about 100° C. The pressure employed in the polymerization, if any, is usually only sufficient to maintain the reaction mixture in liquid form, although either superatmospheric or subatmospheric pressures can be used. The concentration of polymerizable monomer in the polymerizable mixture can be varied widely with concentrations up to about 80 percent by weight, and preferably from about 10 to about 50 percent by weight, based on the weight of the mixture, being satisfactory. Suitable catalysts for the polymerization reaction include, for example, from about 0.001 to about 2.0 weight percent of free radical catalysts, such as 2,2'-azobis(2-methylpropionitrile), hydrogen peroxide, cumene hydroperoxide and the like. In redox polymerization systems, the usual ingredients can be employed. If desired, the polymer can be isolated from the reaction vehicle by freezing, salting out, concentration, precipitation in a non-solvent, such as diethyl ether, or any other procedure suitable for this purpose.

As indicated in U.S. Pat. No. 3,142,568, issued July 28, 1964, it is sometimes advantageous to include a surface active agent or compatible mixtures of such agents in emulsion or suspension preparation of vinyl or addition polymers. Suitable wetting agents include the nonionic, ionic and amphoteric types. Such wetting agents are disclosed, for example, in U.S. Pat. Nos. 2,600,831, issued June 17, 1952; 2,271,622, issued Feb. 3, 1942; 2,271,623, issued Feb. 3, 1942; 2,275,727, issued Mar. 10, 1942; 2,787,604, issued Apr. 2, 1957; 2,816,920, issued Dec. 17, 1957 and 2,739,891, issued Mar. 27, 1956.

The molecular weights of the polymers of the present invention are subject to wide variation, but typically are within the range of from about 10,000 to about 1,000,000. These polymers typically have inherent viscosities within the range of from about 0.1 to about 2.0, and preferably from about 0.2 to about 1.4, as measured (unless otherwise indicated) in a 1:1 (weight) phenolchlorobenzene mixture (0.25 g polymer per 100 ml solution) at 25° C. As used herein, the term "inherent viscosity" is determined by the formula:

$$\eta_{inh} = 2.30 \log \eta_{rel}/C$$

wherein:

$\eta_{inh}$ is the inherent viscosity;

$\eta_{rel}$ is the relative viscosity of a phenolchlorobenzene solution of the polymer; and C is the concentration in grams of polymer per 100 ml of solution.

The polymers of the present invention typically have glass transition temperatures within the range of from about −10° to about 150° C. These temperatures can be determined by differential scanning colorimetry, as disclosed in *Techniques and Methods of Polymer Evaluation*, Volume 2, Marcel Dekker, Inc., N.Y., 1970.

The polymers of the present invention are soluble in a variety of organic solvents, including acetone, tetrahydrofuran, dichloromethane, chloroform, N,N-dimethylformamide, 2-methoxyethanol, dimethyl sulfoxide, p-dioxane and the like. By solubility of the polymer, it is meant that the crosslinking of the polymer results in a distinct solubility differential in organic solvents such that said solvents will dissolve uncrosslinked polymer but not crosslinked polymer.

This invention is further illustrated by the following examples, although it will be understood that these examples are included merely for purposes of illustration and are not intended to limit the scope of the invention.

Examples 1 through 3 illustrate the preparation of some of the polymerizable aldehyde-containing monomers of the present invention.

EXAMPLE 1

Preparation of o-Formylphenyl Vinylbenzyl Ether

A mixture of 235 g (1.53 mol) of vinylbenzyl chloride, 183 g (1.5 mole) of salicylaldehyde, 108.0 g of 85 percent potassium hydroxide, 2.4 g of m-dinitrobenzene, and 3.5 liters of 3A (denatured) ethanol was heated at reflux for approximately 20 hours at about 80° C. The mixture was cooled, filtered and the filtrate was concentrated to an oily solid. The residue was treated with ether and filtered. The filtrate was then washed two times with 5 percent sodium hydroxide and two times with water. The organic phase was dried over sodium sulfate, concentrated to an oil and distilled. The yield of o-formylphenyl vinylbenzyl ether was 149 g (41.5 percent of theory). bp=124° to 130° C./6μ.

The product can also be obtained by recrystallization from ether and dry ice bath cooling.

EXAMPLE 2

Preparation of p-Formylphenyl Vinylbenzyl Ether

By employing the method and two-thirds of the quantities of Example 1, substituting p-hydroxybenzaldehyde for salicylaldehyde, and purifying the reaction product by recrystallization from isopropanol and t-butanol, 15.8 g (6.6 percent of theory) of p-formylphenyl vinylbenzyl ether were obtained. mp=77° to 80° C.

EXAMPLE 3

Preparation of m-Formylphenyl Vinylbenzyl Ether

A mixture of 30.0 g (0.245 mol) of m-hydroxybenzaldehyde, 38.4 (0.251 mol) of vinylbenzyl chloride, 17.6 g of 85 percent potassium hydroxide, 0.4 g of m-dinitrobenzene and 570 ml of 3A alcohol was heated at reflux for 18.25 hours. The mixture was cooled, filtered and the filtrate was concentrated. The residue was treated with ether and filtered. The filtrate was washed three times with 5 percent sodium hydroxide and two times with water. The organic phase was dried over sodium sulfate and concentrated to an oil. The oil was distilled in the presence of m-dinitrobenzene inhibitor. The yield of m-formylphenyl vinylbenzyl ether was 26.0 g (44.5 percent of theory). bp=104°-119° C./3.0–10.0μ.

Preparations 1 through 4 illustrate the preparation of homopolymers from some aldehyde-containing polymerizable monomers.

PREPARATION 1

Solution Polymerization of o-Formylphenyl Vinylbenzyl Ether

A solution of 5.0 g of o-formylphenyl vinylbenzyl ether and 20 ml of p-dioxane was purged with nitrogen. 2,2'-Azobis(2-methylpropionitrile) (0.025 g) was added, and the solution was heated in a 60° C. bath with nitrogen bubbling for 21 hours. The resultant solution was poured into diethyl ether to precipitate polymer, which was subsequently washed with ether and dried in vacuo. The yield of polymer was 2.9 g (58.0 percent of theory). The inherent viscosity of the polymer was 0.22 ((as measured at 25 percent in a 1:1 (weight) solution of phenol and chlorobenzene)), and the Tg was 52° C. The polymer was soluble in tetrahydrofuran.

PREPARATION 2

Solution Polymerization of p-Formylphenyl Vinylbenzyl Ether p-Formylphenyl vinylbenzyl ether was polymerized by a method like that of Preparation 1. The resulting polymer had an inherent viscosity of 0.19. The polymer was soluble in tetrahydrofuran. The yield was 30.0 percent of theory.

PREPARATION 3

Solution Polymerization of m-Formylphenyl Vinylbenzyl Ether

A solution of 5.0 g of m-formylphenyl vinylbenzyl ether and 5 ml of p-dioxane was purged with nitrogen. 2,2'-Azobis(2-methylpropionitrile) (0.0125 g) was added, and the solution was heated in a 60° C. bath with nitrogen bubbling for 16 hours. The solution was then poured into diethyl ether to precipitate the resulting polymer which was collected and dried in vacuo. The yield of polymer was 1.0 g (20.0 percent of theory). The polymer had an inherent viscosity of 0.26, a glass transition temperature of −4° C. and was soluble in tetrahydrofuran.

PREPARATION 4

Emulsion Polymerization of p-Formylphenyl Vinylbenzyl Ether

An emulsion of 23.0 g (0.096 moles) of p-formylphenyl vinylbenzyl ether, 1.15 g of Duponol ME surfactant (Tradename of E. I. duPont de Nemours) and 69.0 g of distilled water was purged with N$_2$ and, thereafter, 0.1 g of K$_2$S$_2$O$_8$ and 0.033 g NaHSO$_3$ were added while stirring. The emulsion was heated in a 60° C. bath for 2.5 hours under N$_2$ with continuous stirring. It was filtered through glass wool to remove an orange-brown precipitate, giving 85.2 g of latex. A sample of this latex was frozen, thawed and filtered to collect the resulting polymer. The polymer was washed with water and dried in a vacuum oven. The solids concentration was determined to be 26.0 percent, which corresponded to 85.5 percent conversion.

Examples 4 through 11 illustrate the preparation of some of the copolymers of the present invention.

EXAMPLE 4

Solution of Polymerization of o-Formylphenyl Vinylbenzyl Ether and N-1-Butyl-N-4-Methacryloylsulfanilamide A mixture of 4.76 g (0.02 mol) of o-formylphenyl vinylbenzyl ether, 5.93 g (0.02 mol) of N-1-butyl-N-4-methacryloylsulfanilamide and 40 ml of p-dioxane was purged with nitrogen. 2,2'-Azobis(2-methylpropionitrile) (0.05 g) was added, and the mixture was heated in a 60° C. bath with nitrogen bubbling. A solution resulted at 60° C. After approximately 21 hours, the solution was poured into diethyl ether to precipitate the resulting polymer. The polymer was collected, washed with ether and dried in vacuo. The polymer had an inherent viscosity of 0.52, a Tg of 94° C. and was soluble in acetone. The yield was 8.8 g (82.3 percent of theory).

EXAMPLE 5

Solution Copolymerization of o-Formylphenyl Vinylbenzyl Ether and Methyl Methacrylate A mixture of 4.76 g (0.02 mol) of o-formylphenyl vinylbenzyl ether, 2.0 g (0.02 mol) of methyl methacrylate and 25 ml of p-dioxane was purged with nitrogen. 2,2'-Azobis(2-methylpropionitrile) (0.034 g) was added, and the resulting solution was heated in a 60° C. bath with nitrogen bubbling for 18 hours. The solution was then poured into diethyl ether and the resulting precipitated polymer was isolated and dried. A yield of 3.2 g (47.4 percent of theory) was obtained.

The polymer had an inherent viscosity of 0.40 and a Tg of 60° C. It was soluble in tetrahydrofuran and dichloromethane.

Other copolymers of o-formylphenyl vinylbenzyl ether and various comonomers were prepared in similar fashion to the copolymers of Examples 4 and 5. These copolymers are listed along with several properties in Table I below.

TABLE I

| | | Polymer Properties | | |
|---|---|---|---|---|
| Reference | Comonomer | I.V. | Tg (°C.) | Soluble In |
| Example 6 | N-(p-tolylsulfonyl)-carbamic acid(maleinimido)methyl ester | 0.71 | 63 | acetone |
| Example 7 | methyl vinyl ketone | 0.62 | 58 | tetrahydrofuran |
| Example 8 | N-butyl-4-methacryloyloxybenzenesulfonamide | 0.59 | 61 | acetone |
| Example 9 | N-1-ethyl-N-4-methacryloylsulfanilamide | 0.26 | 56 | acetone |

EXAMPLE 10

Terpolymerization of o-Formylphenyl Vinylbenzyl Ether, N-(2,6-Dihydroxyphenyl)acrylamide, and 2-(Methacryloyloxy)ethyltrimethylammonium Methosulfate A solution of 1.19 g (0.005 mole) of o-formylphenyl vinylbenzyl ether, 3.58 g (0.020 mole) of N-(2,6-dihydroxyphenyl)acrylamide, 7.08 g (0.025 mole) of 2-(methacryloyloxy)ethyltrimethylammonium methosulfate and 107 ml of N,N-dimethylformamide was purged with nitrogen. 2,2'-Azobis(2-methylpropionitrile) (0.118 g) was added, and the solution was heated in a 60° C. bath with nitrogen bubbling for approximately 21 hours. The solution was poured into acetone to precipitate polymer, which was collected and dried at room temperature, in vacuo. The yield of polymer was 12.1 g (100 percent conversion plus retained solvent). The inherent viscosity was determined to be 2.52 (in water), and the glass transition temperature on second heating was 103° C.

EXAMPLE 11

Copolymerization of o-Formylphenyl Vinylbenzyl Ether and 2-(Methacryloyloxy)ethyltrimethylammonium Methosulfate A solution of 8.51 g (0.03 mole) of 2-(methacryloyloxy)ethyltrimethylammonium methosulfate, 2.38 g (0.01 mole) of o-formylphenyl vinylbenzyl ether, and 98 ml of N,N-dimethylformamide was purged with nitrogen. 2,2'-Azobis(2-methylpropionitrile) (0.054 g) was added, and the solution was heated in a 60° C. bath for 19 hours. The solution was poured into ether to precipitate polymer, which was rinsed again with ether and partially dried. The polymer was dissolved in methanol, reprecipitated into ether, isolated and dried in vacuo. The yield of polymer was 8.4 g (77.1 percent conversion). The inherent viscosity was determined to be 1.09 (in DMF), and the glass transition temperature was found to be 97° C. on third heating.

EXAMPLE 12

This example demonstrates how the polymers of the present invention can be used in elements from which negative relief images can be made.

In 1.8 g of a 10 percent solution of poly(o-formylphenyl vinylbenzyl ether) in A.C.S. grade tetrahydrofuran (THF) were dissolved 20 mg of 2-isopropoxy-1,4-naphthoquinone, a photactivator, and 5 mg of 2,2'-bipyridine. To this was added a solution of 20 mg [(NH$_2$[CH$_2$]$_3$NH$_2$)Co](CF$_3$CO$_2$)$_3$ ((tris(trimethylenediamine) cobalt(III) trifluoroacetate)) in 200 mg of 2-methoxyethanol. This dope was coated with a 100-micron doctor blade on subbed poly(ethylene terephthalate) support. The dried coating was given an exposure of 3200 erg/cm$^2$ at 320 nm and heated for 10 seconds, coating side up, on a 90° C. hot block. Exposure was achieved by using a monochromatic spectral sensitometer that allows the isolation of comparatively narrow bands of the spectrum and a determination of the photographic response to the material to the radiation of the spectral region selected. The output radiation from an air-cooled, water-filtered, 1000-watt, high-pressure Xenon lamp was passed through quartz optics and was focused upon the entrance slits of a Bausch and Lomb ¼-meter, high-intensity monochromator. The output of the monochromator was filtered with broad bandpass filters to remove higher order radiation, passed through a Uniblitz electronic shutter and finally impinged upon the photographic material. As the irradiation area of the material was small, the exposures corresponding to the different steps of a sensitometric step tablet could not be made at the same time, but were made in succession with the exposure, being time-modulated to produce the range of exposures required. To compute the irradiance of the sensitometer, it was necessary first to determine wavelength regions at which the exposure was to be made. The irradiance per unit time was measured at a given exposure distance with a Hewlett-Packard Flux Meter, Model 8330A, and a Hewlett-Packard Flux Detector, Model 8334A. The 320 nm exposure of this example was conducted at a wavelength very close to the $\lambda_{max}$ of the 2-isopropoxy-1,4-naphthoquinone ($\lambda_{max}$=327 nm) for an amount of time required to give an exposure of 3200 ergs per square centimeter.

The coating was then immersed in an agitated mixture of 2:1, by volume, THF:p-dioxane. The unexposed areas were removed, leaving a relief negative image.

Although the present invention has been described in considerable detail with reference to certain preferred embodiments thereof, it will be understood that variations and modifications can be effected without departing from the spirit and scope of the invention.

What is claimed is:

1. A compound having the formula (I):

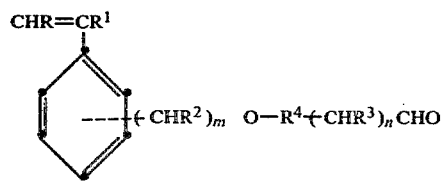

wherein:
R, R$^1$, R$^2$ and R$^3$ are independently hydrogen or alkyl containing from 1 to 4 carbon atoms;
R$^4$ is arylene containing 6 to 18 carbon atoms;
m is an integer from 1 to 4; and
n is an integer from 0 to 4.

2. The compound of claim 1 wherein R, R$^1$, R$^2$ and R$^3$ are hydrogen.

3. The compound of claim 2 wherein m is 1 and n is 0.

4. The compound of claim 3 wherein R$^4$ is phenylene.

5. A method of making the compound of claim 1 comprising reacting, in the presence of an acid acceptor, a compound having the formula:

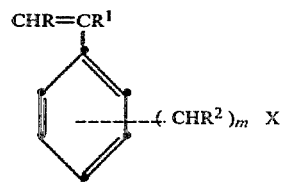

with a compound having the formula HO—R$^4$—CHR$^3$)$_n$CHO, wherein:
X is halide;
R, R$^1$, R$^2$ and R$^3$ are independently hydrogen or alkyl containing from 1 to 4 carbon atoms;

$R^4$ is arylene containing 6 to 18 carbon atoms;

m is an integer from 1 to 4; and n is an integer from 0 to 4.

6. The method of claim 5 wherein R, $R^1$, $R^2$ and $R^3$ are hydrogen.

7. The method of claim 6 wherein m is 1 and n is 0.

8. The method of claim 7 wherein $R^4$ is phenylene.

9. The method of claim 5 wherein the reaction is carried out at a temperature of from about 70° to about 90° C. at about atmospheric pressure.

10. The method of claim 5 wherein the starting molar ratio of the compound having the formula:

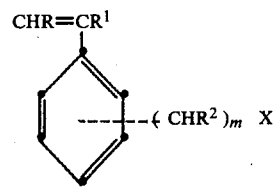

to the compound having the formula HO—$R^4$—$CHR^3)_n$CHO is from about 1:0.09 to about 1:1.1.

11. The method of claim 5 wherein the acid acceptor is an hydroxide.